United States Patent [19]

Schmidt et al.

[11] Patent Number: 4,578,476

[45] Date of Patent: Mar. 25, 1986

[54] PROCESS FOR THE PRODUCTION OF 2-ARYL-4-ACYL-1.3.4-OXDIAZOLONES-(5)

[75] Inventors: Manfred Schmidt; Karl-Heinrich Meyer, both of Krefeld, Fed. Rep. of Germany

[73] Assignee: Bayer Aktiengesellschaft, Leverkusen, Fed. Rep. of Germany

[21] Appl. No.: 621,934

[22] Filed: Jun. 18, 1984

[30] Foreign Application Priority Data

Jun. 28, 1983 [DE] Fed. Rep. of Germany ....... 3323283

[51] Int. Cl.$^4$ .................... C07D 271/10; C08J 9/10
[52] U.S. Cl. ........................ 548/144; 521/90; 521/180; 521/182; 521/184
[58] Field of Search ............................... 548/144

[56] References Cited

U.S. PATENT DOCUMENTS 3,410,863  11/1968  Boesch et al. .
3,941,798  3/1976   Fort et al. ............................ 548/144
4,500,653  2/1985   Schmidt et al. ....................... 521/90

OTHER PUBLICATIONS

Chem. Ber. 82, pp. 121–123, (1949).
Schmidt et al., Chem. Abst. 102-204918q.
Schmidt et al., Chem. Abst. 102-185087z.
Chemical Abstracts, vol. 98, No. 8, 21, Feb., 1983, 54598t.
Chemical Abstracts, vol. 98, No. 18, 2, May, 1983, 143927s.
Chemical Abstracts, vol. 91, No. 19, 5, Nov., 1979, 156918v.

*Primary Examiner*—Donald G. Daus
*Assistant Examiner*—Cecilia Shen
*Attorney, Agent, or Firm*—Connolly and Hutz

[57] ABSTRACT

A process for the production of 2-aryl-4-acyl-1.3.4-oxdiazolones-(5), in which an aromatic carboxylic acid hydrazide is reacted at a pH value of from 1.8 to 3.0 with phosgene in a mixture consisting of water and acetone at a temperature of from 0° C. to 50° C., subsequently the pH is increased to from 9.5 to 11.0, then about 100 mol % of a carboxylic acid chloride or about 50 mol % of a dicarboxylic acid chloride (based on mols of carboxylic acid hydrazide) is added and optionally from $10^{-4}$ to 1.0 mol % (based on mols of carboxylic acid hydrazide) of a tertiary amine or phosphine is added as a catalyst and the reaction is completed at a temperature from 0° C. to 50° C.

3 Claims, No Drawings

PROCESS FOR THE PRODUCTION OF 2-ARYL-4-ACYL-1.3.4-OXDIAZOLONES-(5)

This invention relates to a process for the production of 2-Aryl-4-acyl-1.3.4-oxidiazolones-(5) and in particular a process for the production of oxdiazolones corresponding to the formula (I):

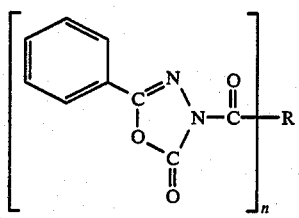

wherein
R represents n-valent $C_1$–$C_{18}$-alkyl, $C_1$–$C_{18}$-alkoxy, $C_6$–$C_{12}$-cycloalkyl, $C_6$–$C_{12}$-cycloalkoxy, $C_2$–$C_{18}$-alkenyl, $C_6$–$C_{18}$-cycloalkoxy, $C_6$–$C_{18}$-aryl, $C_6$–$C_{12}$-aryloxy, $C_7$–$C_{18}$-arylalkyl, $C_7$–$C_{18}$-arylalkyloxy, $C_7$–$C_{18}$-alkylaryloxy and $C_7$–$C_{18}$-alkylaryloxy radicals and
n represents 1 or 2.

Oxdiazolones may be used as blowing agents for the production of structural foams of heat resistant plastics such as polycarbonates, polyestercarbonates, aromatic polyesters based on bisphenols and iso-terephthalic acid, polysulfones, liquid-crystalline aromatic polyesters having an anistropic melting phase, polyethylene terephthalate, polybutylene terephthalate, polystyrene, ABS-plastics materials and mixtures thereof. The decomposition temperature of the oxdiazolones is determined by the radical R so that the blowing agents may be selected according to the processing temperature of the plastic materials to be foamed.

As decomposition products carbon dioxide and 1.3.4-oxdiazoles (II) are generated as shown by the following equation

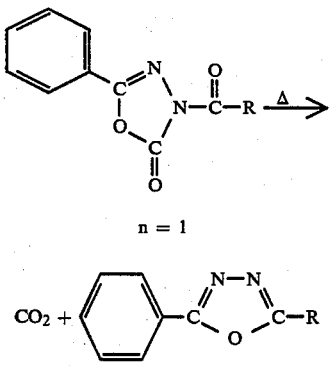

The production of 2-phenyl-1.3.4-oxdiazolone-(5) is described in Chem. Ber. 82, P. 121–123 (1949). To this end, an acid hydrazide is reacted with phosgene in aqueous solution. The process may also be used for 2-alkyl-substituted oxidazolones. The reaction of several oxdiazolones in pyridine with benzoyl chloride to produce the corresponding 4-acyl-derivatives is also described in the specified literature.

Object of this invention is an improved process for the production of 2-aryl-4-acyl-1.3.4-oxdiazolones-(5) wherein an aromatic carboxylic acid hydrazide is reacted at a pH value of from 1.8 to 3 with phosgene in a mixture of water and acetone at a temperature of from 0° C. to 50° C., subsequently the pH value is increased to the range of 9.5 to 11 and about 100 mol % of a carboxylic acid chloride or about 50 mol % of dicarboxylic acid chloride (based on 100 mol % of carboxylic acid hydrazide) is added, and optionally from $10^{-4}$ to 1 mol % (based on 100 ml % of carboxylic acid hydrazide) of a tertiary amine or phosphine as a catalyst is added and the reaction is allowed to proceed to completion at from 0° C. to 50° C.

The following are examples of suitable aromatic carboxylic acid hydrazides: benzoic acid hydrazide and hydrazides of naphthoic acids, benzoic acid hydrazide being preferred.

By way of example, compounds corresponding to formulae III and IV may be used as carboxylic acid chlorides or dicarboxylic acid chlorides.

wherein $R_1$ represents $C_1$–$C_{18}$alkyl, alkoxy, $C_6$–$C_{12}$ cycloalkyl, cycloalkyloxy, $C_2$–$C_{18}$ alkenyl, alkenyloxy, $C_6$–$C_{18}$ aryl, aryloxy, $C_7$–$C_{18}$ arylalkyl, arylalkyloxy, alkylaryl and alkylaryloxy,

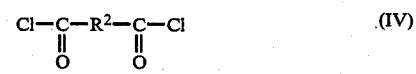

wherein $R^2$ represents a single bond, $C_1$–$C_{12}$ alkyl, $C_2$–$C_{12}$ alkyloxy, $C_6$–$C_{18}$ aryl or aryloxy.

The following are particularly suitable carboxylic acid chlorides or dicarboxylic acid chlorides: benzoic acid chloride, naphthoic acid chlorides, isophthalic acid dichloride, terephthalate acid dichloride, succinic acid dichloride, oxalic acid dichloride and malonic acid dichloride.

The following are particularly suitable chlorocarbonic esters corresponding to formula III or bischlorocarbonic esters corresponding to formula IV: chlorocarbonic acid phenyl esters, -ethyl esters, -propyl ester, and the bis-chlorocarbonic esters of bis-phenol A.

The process according to the present invention will now be described in more detail with reference to an example.

Benzoic acid hydrazide is suspended in from 4 to 8 times its quantity by weight of a water/acetone mixture. A 10 to 20% by weight excess of phosgene is introduced into the well stirred suspension which is cooled to 10° C. to 25° C. The pH value is maintained at from 1.8 to 3.0 by addition of an aqueous solution of sodium hydroxide. The phosgene can be introduced at atmospheric pressure by using a cooler which contains dry ice/methanol as a cooling agent or according to the preferred method by using a sealed pressure apparatus. When the phosgene has been completely introduced, from $10^{-4}$ to 1 mol % (based on mols benzoic acid hydrazide) of a tertiary amine such as triethylamine, N-ethylpiperidine, diazabicyclooctane or of a tertiary phosphine such as triphenylphosphine or a $C_4$–$C_8$ trialkylphosphine are added and the pH value is adjusted with an aqueous solution of sodium hydroxide to form 9.5 to 11.0. The NaOH quantity which is used must be at least equimolar to the quantity of benzoic acid hydrazide which is used. With cooling (reaction temperature maximum 25° C.), an acetone solution (ca. 50% by weight) of 100 mol % based on benzoic acid hydrazide of an acyl chloride corresponding to the general structure (III) or a acetone solution (ca. 50% by weight) of 50 mol % of a bisacyldichloride corresponding to the general structure (IV) is introduced into the reaction mixture and the reaction is subsequently completed by stirring at room temperature.

This causes the pH value to drop to 6.8 to 7.7. The reaction product is isolated by filtration, washed with water until it is free of chloride and is dried under vacuum at from 50° to 100° C.

The resulting yields are ≧93% of the expected yield of 2-aryl-4-acyl-1.3.4-oxodiazolone-(5)-derivatives corresponding to the general structure (I).

EXAMPLE 1

The synthesis of di-[2-phenyl-1.3.4-oxdiazolone-(5)-]-4-terephthalamide.

50 g (0.368 mols) of benzoic acid hydrazide (mp. 112° C.) are suspended in 150 ml of acetone and 100 ml of water with stirring. With cooling (internal temperature: from 10° to 20° C.) 41.8 g (0.438 mols) of phosgene ( 19 mol % excess) are introduced into the suspension, the pH of the reaction mixture being maintained at from 2 to 2.5 by simultaneous successive addition of an 45% aqueous sodium hydroxide solution (ca. 70 ml) over a period of 20 minutes. The solution is subsequently allowed to react for ½ hr. with the introduction of $N_2$ and with intensive stirring. The pH is adjusted to from 10–10.5 by the addition of an 45% aqueous sodium hydroxide solution (ca. from 35 to 36 g) to the suspension of colourless crystals in aqueous acetone and the internal temperature is reduced to from 10°–15° C. After 0.014 g of triethylamine have been added, a 50% solution of 37.34 g (0.184 mols) of terephthalic acid dichloride in acetone is introduced over a period of 20 mins with intensive stirring, the internal temperature being maintained at from 10° to 15° C. by cooling. During the course of this the pH falls to from 6.8 to 7.1. The solution is allowed to subsequently react for 2 hours at room temperature and the reaction product is isolated by filtration. The colourless crystals are washed with warm water until they are free of chloride and are dried under vacuum at from 80° C. to 100° C.

Yield: 78 g ( 93% of the theoretical yield).
Mp.=282° C.
Decomp. Temp.=285° C.
Insoluble in alcohols, dioxane, ethylacetate, monochlorobenzene and acetone.

EXAMPLE 2

Synthesis of the 2-phenyl-4-acetyl-1.3.4-oxdiazolone-(5)

50 g (0.368 mols) of benzoic acid hydrazide are suspended in 50 ml of acetone and 150 ml of water with stirring. While cooling (internal temperature: from 10° to 20° C.), 41.8 g (0.438 mols) of phosgene (=19 mol % excess) are introduced into the suspension, the pH value of the reaction mixture being maintained at from 1.8 to 2.0 by simultaneous successive addition an 45% aqueous sodium hydroxide solution (ca. 70 ml). The solution is subsequently allowed to react for ½ hr. at room temperature and the pH value of the suspension is adjusted to 10.5 by addition of 36 g of an 45% aqueous sodium hydroxide solution. The internal temperature is lowered to 10° C. by cooling, and subsequently after 0.02 g N-ethylpiperidine have been added, a solution of 28.89 g (=0.368 mols) of acetyl chloride in 30 ml of acetone are added over a period of 20 mins. The solution is allowed to subsequently react for 1 hr., the internal temperature rising to 20° C. and the pH value increasing to 7.1. The reaction product is filtered off, washed with water until it is free of chloride and is dried under vacuum at 80° C.

Yield: 71.32 g ( 95% of the theoretical yield).
Mp. 114° C.
Decomposition point: 200° C.

EXAMPLE 3

Synthesis of 2-phenyl-4-phenoxycarbonyl-1.3.4-oxdiazolone-(5)

50 g (0.368 mols) of benzoic acid hydrazide are suspended in 30 ml of acetone and in 180 ml of water with stirring. While cooling (internal temperature 10°–20° C.), 41.0 g (0.430 mols) of phosgene (=18.6 mol % excess) are introduced into the suspension, the pH value of the reaction mixture being maintained at from 1.8 to 2.0 by simultaneously metered addition of an 40% aqueous sodium hydroxide solution (ca. 78 ml). The solution is subsequently reacted for ½ hr. at room temperature and the pH value of the suspension is adjusted to 10.5 by addition of 36 g of an 45% aqueous sodium hydroxide solution. The internal temperature is lowered to 10° C. by cooling. After 0.05 g of triphenylphosphine have been added, a solution of 57.59 g (0.368 mols) of chloroformic acid phenylester in 60 ml of acetone are added over a period of 30 mins. The solution is subsequently allowed to react for 2 hrs., the internal temperature rising to 25° C. and the pH value increasing to 6.9. The reaction product is filtered off, washed with water until it is free of chloride and dried under vacuum at 100° C.

Yield: 101.7 g ( 96% of the theoretical yield).
Mp.=147° C.
Decomposition temperature=286° C.

We claim:

1. A process for the production of 2-aryl-4-acyl-1.3.4 oxdiazolones-(5) which comprises reacting an aromatic carboxylic acid hydrazide at a pH value of from 1.8 to 3.0 with phosgene in a mixture consisting of water and acetone as a solvent at a temperature of from 0° C. to 50° C., subsequently increasing the pH value to a range of 9.5 to 11.0 and adding about 100 mol % of a carboxylic acid chloride or about 50 mol % of a dicarboxylic acid chloride (based on 100 mol % of carboxylic acid hydrazide) and allowing the reaction to proceed to completion at from 0° C. to 50° C.

2. A process according to claim 1, wherein said aromatic carboxylic acid hydrazide is benzoic acid hydrazide.

3. A process according to claim 1, wherein the reaction is carried out in the presence of a catalyst comprising a tertiary amine or a tertiary phosphine.

* * * * *